US006351663B1

(12) United States Patent
Flower et al.

(10) Patent No.: US 6,351,663 B1
(45) Date of Patent: Feb. 26, 2002

(54) METHODS FOR DIAGNOSING AND TREATING CONDITIONS ASSOCIATED WITH ABNORMAL VASCULATURE USING FLUORESCENT DYE ANGIOGRAPHY AND DYE-ENHANCED PHOTOCOAGULATION

(75) Inventors: Robert W. Flower, Hunt Valley, MD (US); Abu Alam, Lake Forest, IL (US)

(73) Assignee: Akorn, Inc., Buffalo Grove, IL (US)

( * ) Notice: Subject to any disclaimer, the term of this patent is extended or adjusted under 35 U.S.C. 154(b) by 0 days.

(21) Appl. No.: 09/393,456

(22) Filed: Sep. 10, 1999

(51) Int. Cl.$^7$ .................................................. A61B 6/00
(52) U.S. Cl. ..................... 600/476; 600/431; 250/459.1
(58) Field of Search ............................... 600/431, 473, 600/476, 160, 182; 606/4, 10, 13, 15; 604/19; 382/130; 250/459.1

(56) References Cited

U.S. PATENT DOCUMENTS

| 2,895,955 | A |   | 7/1959  | Heseltine et al. |
| 3,736,524 | A |   | 5/1973  | Drexhage |
| 3,871,772 | A |   | 3/1975  | Munnerlyn et al. |
| 3,893,447 | A |   | 7/1975  | Hochheimer et al. |
| 3,944,341 | A |   | 3/1976  | Pomerantzeff |
| 4,056,310 | A |   | 11/1977 | Shimizu et al. |
| 4,251,139 | A |   | 2/1981  | Matsumura |
| 4,369,250 | A |   | 1/1983  | Gindler |
| 4,412,543 | A |   | 11/1983 | Vassiliadis et al. |
| 4,466,442 | A |   | 8/1984  | Hilmann et al. |
| 4,541,438 | A |   | 9/1985  | Parker et al. |
| 4,573,778 | A |   | 3/1986  | Shapiro |
| 4,608,990 | A |   | 9/1986  | Elings |
| 4,762,701 | A |   | 8/1988  | Horan et al. |
| 4,786,813 | A |   | 11/1988 | Svanberg et al. |
| 4,799,783 | A |   | 1/1989  | Takahashi et al. |
| 4,821,117 | A |   | 4/1989  | Sekiguchi |
| 4,835,103 | A |   | 5/1989  | Cercek et al. |
| 4,842,401 | A |   | 6/1989  | Maurice |
| 4,859,584 | A |   | 8/1989  | Horan et al. |
| 4,957,481 | A | * | 9/1990  | Gatenby |
| 4,978,213 | A |   | 12/1990 | El Hage |
| 5,072,731 | A |   | 12/1991 | Taratuta et al. |
| 5,092,331 | A |   | 3/1992  | Nakamura et al. |
| 5,116,114 | A |   | 5/1992  | Nakamura |
| 5,126,235 | A |   | 6/1992  | Hioki |
| 5,141,303 | A |   | 8/1992  | Yamamoto et al. |
| 5,150,292 | A |   | 9/1992  | Hoffmann et al. |
| 5,163,437 | A |   | 11/1992 | Fujii et al. |
| 5,225,859 | A |   | 7/1993  | Fleischman |
| 5,247,318 | A |   | 9/1993  | Suzuki |
| 5,277,913 | A |   | 1/1994  | Thompson et al. |
| 5,279,298 | A |   | 1/1994  | Flower |
| 5,292,362 | A |   | 3/1994  | Bass et al. |
| 5,303,709 | A |   | 4/1994  | Dreher et al. |
| 5,315,998 | A |   | 5/1994  | Tachibana et al. |
| 5,346,689 | A | * | 9/1994  | Peyman et al. |
| 5,394,199 | A |   | 2/1995  | Flower |
| 5,400,791 | A |   | 3/1995  | Schlier et al. |
| 5,438,989 | A |   | 8/1995  | Haglund et al. |
| 5,441,858 | A |   | 8/1995  | Delprato et al. |
| 5,450,144 | A |   | 9/1995  | Ben Nun |
| 5,552,452 | A |   | 9/1996  | Khadem et al. |
| 5,569,587 | A |   | 10/1996 | Waggoner et al. |
| 5,573,750 | A |   | 11/1996 | Singh |
| 5,576,013 | A |   | 11/1996 | Williams et al. |
| 5,618,733 | A |   | 4/1997  | Sakata et al. |
| 5,624,597 | A |   | 4/1997  | Buhl et al. |
| 5,643,356 | A |   | 7/1997  | Nohr et al. |
| 5,648,062 | A |   | 7/1997  | Klaveness et al. |
| 5,676,928 | A |   | 10/1997 | Klaveness et al. |
| 5,691,204 | A |   | 11/1997 | Kantor et al. |
| 5,707,608 | A |   | 1/1998  | Liu |
| 5,707,986 | A |   | 1/1998  | Miller et al. |
| 5,716,642 | A |   | 2/1998  | Bagchi et al. |
| 5,719,027 | A |   | 2/1998  | Miyazaki et al. |
| 5,747,475 | A |   | 5/1998  | Nordquist et al. |
| 5,750,722 | A |   | 5/1998  | Huynh et al. |
| 5,762,957 | A |   | 6/1998  | Mehlhorn |
| 5,773,299 | A |   | 6/1998  | Kim et al. |
| 5,798,349 | A |   | 8/1998  | Levy et al. |
| 5,804,448 | A |   | 9/1998  | Wang et al. |

FOREIGN PATENT DOCUMENTS

| DE | 3124305     |   | 1/1983  |
| DE | 3926652     |   | 4/1991  |
| EP | 0109846     |   | 5/1984  |
| EP | 0554643     |   | 8/1993  |
| EP | 0649667     |   | 4/1995  |
| EP | 0791361     | A | 8/1997  |
| EP | 589825      |   | 5/1998  |
| GB | 1048419     |   | 11/1966 |
| GB | 2034916     |   | 6/1980  |
| GB | 244492      |   | 4/1987  |
| JP | 87042892    |   | 9/1987  |
| WO | 95/24930    |   | 9/1995  |
| WO | 96/31237    |   | 12/1996 |
| WO | 97/31582    |   | 9/1997  |
| WO | 97/33620    |   | 9/1997  |
| WO | 97/46262    | A | 12/1997 |
| WO | 00/41726    | A | 7/2000  |

OTHER PUBLICATIONS

"Photosensitizer," *Ophthamalmic Surgery and Lasers*, vol. 28, No. 5, p 410 (1997).

Desmettre et al., "Diode Laser–Induced Thermal Damage Evaluation on the Retina with a Liposome Dye System," *Lasers in Surgery and Medicine*, vol. 24, pp. 61–68 (1999).

Flower et al., "Evolution of Indocyanine Green Dye Choroidal Angiography," *Optical Engineering*, vol. 34, No. 3, pp. 727–736 (1995).

(List continued on next page.)

*Primary Examiner*—Marvin M. Lateef
*Assistant Examiner*—Shawna J Shaw
(74) *Attorney, Agent, or Firm*—Leydig, Voit & Mayer, Ltd.

(57) ABSTRACT

Methods concerning medical uses for fluorescent dyes, e.g., Indocyanine green (ICG), fluorescein, rose bengal, for diagnosis and treatment. Methods for enhancing the clarity of fluorescent dye angiograms using relatively high dye concentrations, methods for determining the direction of blood flow within a blood vessel using fluorescent dye angiograms, and methods of identifying blood vessels that feed a lesion, such as a CNV or tumor. Methods of reducing the flow of blood into lesions incorporating dye-enhanced photocoagulation are also provided.

83 Claims, No Drawings

OTHER PUBLICATIONS

Flower et al., "Pulsatile Flow in the Choroidal Circulation: A Preliminary Investigation," *EYE*, vol. 4, pp. 310–318 (1990).
Flower et al., "Variability in Choriocapillaris Blood Flow Distribution," *Investigative Ophthalmology & Visual Science*, vol. 36, No. 7, pp. 1247–1258 (1995).
Flower, "Choroidal Angiography Today and Tomorrow," *Retina*, vol. 12, No. 3, pp. 189–190 (1992).
Flower, "Extraction of Choriocapillaris Hemodynamic Data from ICG Fluorescence Angiograms," *Investigative Ophthalmology & Visual Science*, vol. 34, No. 9, pp. 2720–2729 (1993).
Flower, "Injection Technique for Indocyanine Green and Sodium Fluorescein Dye Angiography of the Eye," *Investigative Ophthalmology*, vol. 12, No. 12, pp. 881–895 (1973).
Gathje et al., "Stability Studies on Indocyanine Green Dye," *Journal of Applied Physiology*, vol. 29, No. 21, pp. 181–185 (1970).
Holzer et al., "Photostability and Thermal Stability of Indocyanine Green," *J. Photochem. Photobiol. B: Biol.*, vol. 47, pp. 155–164 (1998).
Klein et al., "An Image Processing Approach to Characterizing Choroidal Blood Flow," *Investigative Ophthalmology & Visual Science*, vol. 31, No. 4, pp. 629–637 (1990).
Miki et al., "Computer Assisted Image Analysis Using the Subtraction Method in Indocyanine Green Angiography," *European Journal of Ophthalmology*, vol. 6, No. 1, pp. 30–38 (1996).
DuBosar, "Population at Risk: Age–Related Macular Degeneration," *Ocular Surgery News*, 10 Pages, (May 15, 1998).
Chen et al., "Photothermal Effects on Murine Mammary Tumors Using Indocyanine Green and an 808–nm Diode Laser: an in vivo Efficacy Study," *Cancer Lett.*, vol. 98, No. 2, pp. 169–173 (1996).
Alcon Pharmaceuticals Ltd. "Pharmacyclics Inc.," *The Business and Medicine Report*, p. 63 (Jan. 1998).
Shraga et al., "Feeder Vessel Photocoagulation of Subfoveal Choroidal Neovascularization Secondary to Age–Related Macular Degeneration," *Ophthalmology*, vol. 105, No. 4, pp. 662–669 (1998).
Flower et al., "Clinical Infrared Absorption Angiography of the Choroid," *American Journal of Ophthalmology*, vol. 73, No. 3, pp. 458–459 (1972).
Flower et al., "A Clinical Technique and Apparatus for Simultaneous Angiogrpahy of the Separate Retinal and Choroidal Circulations," *Investigative Ophthalmology*, vol. 12(4), pp. 248–261 (1973).
Hochheimer et al., "Angiography of the Cervix," *Johns Hopkins Medical Journal*, vol. 135, pp. 375–382, (1974).
Flower, "High Speed Human Choroidal Angiography Using Indocyanine Green Dye and a Continuous Light Source," *International Symposium on Fluorescein Angiography, Documenta Ophthmologica Proceedings Series*, vol. 9, pp. 59–64 (1976).
Flower et al., "Indocyanine Green Dye Fluorescence and Infrared Absorption Choroidal Angiography Performed Simultaneously with Fluorescein Angiography," *Johns Hopkins Medical Journal*, vol. 138, No. 2, pp. 33–42 (1976).
Orth et al., "Potential Clinical Applications of Indocyanine Green Choroidal Angiography," *The Eye, Ear, Nose and Throat Monthly*, vol. 55, Jan., pp. 15–28, 58 (1976).
Patz et al., "Clinical Applications of Indocyanine Green Angiography," *International Symposium on Fluorescein Angiography, Documenta Ophthmolgoica*, vol. 9, pp. 245–251 (1976).
Flower, "Choroidal Fluorescent Dye Filling Patterns a Comparison of High Speed Indocyanine Green and Fluorescein Angiograms," *International Ophthalmology*, vol. 2(3), pp. 143–150 (1980).
Hyvarinen et al., "Indocyanine Green Fluorescence Angiography," *ACTA Ophthalmologica*, vol. 58, pp. 528–538 (1980).
Bischoff et al., "Ten Years Experience with Choroidal Angiography Using Indocyanine Green Dye–A New Routine Examination or an Epilogue," *Doc Ophthalmology*, vol. 60(3), pp. 235–291 (1985).
Murphy et al., "Effects of Retinal Photocoagulation on the Choroidal Circulation," *Investigative Ophthalmology & Visual Science*, vol. 32(4), p. 785 (1991) Meeting Abstract.
Murphy et al., "Indocyanine Green Angiographic Studies of Occult Choroidal Neovascularization," *Investigative Ophthalmology & Visual Science*, vol. 43(4), p. 1134 (1993) Meeting Abstract.
Flower, "Binding and Extravasation of Indocyanine Green Dye," *Retina*, vol. 14, No. 13, pp. 283–284 (1994).
Lim et al., "Indocyanine Green Angiography," *International Ophthalmology Clinics*, vol. 35(4), pp. 59–70 (1995).
Hiner et al., "A Previously Undescribed Indocyanine Green Angiographic Filling Pattern," *Investigative Ophthalmology & Visual Science*, vol. 36, No. 4 (1995) Summary Meeting Abstract.
Flower et al., "Disparity Between Fundus Camera and Scanning Laser Ophthalmoscope Indocyanine Green Imaging of Retinal Pigment Epithelium Detachments," *Retina*, vol. 18(3), pp. 260–268 (1998).
Staurenghi et al., "Laser Treatment of Feeder Vessels in Subfoveal Choroidal Neovascular Membranes," *Ophthalmology*, vol. 105, No. 12, pp. 2297–2305 (1998).
Flower et al., "Expanded Hypothesis on the Mechanism of Photodynamic Therapy Action on Choroidal Neovascularization," *Retina*, vol. 19, No. 5 pp. 365–369 (1999).
Flower, "Experimental Studies of Indocyanine Green Dye–Enhanced Photocoagulation of Choroidal Neovascularization Feeder Vessels," *American Journal of Ophthalmology* vol. 129, No. 4, pp. 501–512 (2000).
Mendelson et al., "Amelioration of Experimental Lipid Keratopathy by Photochemically Induced Thrombosis of Feeder Vessels," *Arch Ophthalmol*, vol. 105, Jul. 1987 (pp. 983–988).
Tsilimbaris et al., "Photothrombosis Using Two Different Phthalocyanine Administration Routes: Continuous I.V. Infusion v. Bolus I.V. Injection," *Photochem. Photobiol.*, 62(3), 1995, (pp. 435–441).
Spinelli et al., "Endoscopic Treatment of Gastrointestinal Tumors: Indications and Results of Laser Photocoagulation and Photodynamic Therapy," *Seminars in Surgical Onocology*, 11 (4), 1995, (pp. 307–318) (Abstract only).
Von Kerczek et al., "The Effects of Indocyanine Green Dye–Enhanced Photocoagulation on the Blood Flow in the Choriocapillaris and the Choroidal Neovascularization," *Advances in Heat and Mass Transfer in Biotechnology*, 2000, (pp. 1–3). (Abstract only).

* cited by examiner

METHODS FOR DIAGNOSING AND TREATING CONDITIONS ASSOCIATED WITH ABNORMAL VASCULATURE USING FLUORESCENT DYE ANGIOGRAPHY AND DYE-ENHANCED PHOTOCOAGULATION

FIELD OF THE INVENTION

The present invention relates generally to methods for diagnosing and treating conditions associated with abnormal vasculature.

BACKGROUND OF THE INVENTION

Fluorescent dyes, such as indocyanine green (ICG), have been used for years in connection with angiography to diagnose and treat vascular abnormalities that occur in the eye, e.g., choroidal neovascularization (CNV). CNV is a cause of Age-Related Macular Degeneration (ARMD), which is the leading cause of significant visual impairment in the elderly.

CNV originates in the choroidal blood vessels, the latter lying adjacent the retina of the eye. When CNV forms, it may intrude into and displace a portion of the sensory retina from its normal position, thereby distorting vision. Vision may also be blocked entirely if hemorrhage of the CNV occurs.

One method of diagnosing and treating ARMD is by laser photocoagulation of the CNV. This treatment, however, is successful to the extent that the CNV can be accurately mapped. This is because the CNV is, by definition, in the macular area and often encroaches on the fovea. Application of photocoagulation close to the fovea can result in the destruction of high acuity vision and/or accelerated growth of the CNV.

Generally, mapping of CNV is completed using angiograms. Angiograms are images of blood vessels, obtained by injecting a fluorescent dye into the blood stream prior to obtaining an image. As any of several dyes may be used, and because each dye fluoresces at its own particular wavelength, a radiation source that emits light (radiation) at that particular wavelength (e.g., a low-powered laser provided using fiber optic cables incorporated into a fundus camera) is used to illuminate the eye. Such a light source is part of a fundus camera, which also includes a CCD video camera. At or about the time of dye injection into the animal, the fundus camera begins capturing images, i.e., angiograms, of the eye at specific time intervals. The angiograms provide a record of the extent of dye movement within the ocular vasculature at each specific time interval.

More specifically, after the dye is injected into the body, the dye enters the vasculature of the eye and begins to fluoresce due to the presence of the appropriate excitation radiation (light). The fluorescing dye, being mixed with the ocular blood, provides each angiogram with an accurate illustration of the extent of ocular blood flow through the ocular vasculature at that moment. By comparing a series of angiograms of the same vasculature over a given time period, one is able to map the vasculature and determine the location of a CNV, and may then move to treat this abnormality, e.g., by laser photocoagulation of the CNV itself.

While the foregoing methodology has met with success, several issues remain. One is the clarity of the angiograms obtained using the previously described diagnostic methods. Clearly, any improvements in the angiogram clarity would result in a more accurate diagnosis, and, more significantly, allow a physician to more accurately locate a CNV requiring treatment.

Further, the medical uses of fluorescent dyes outside of the foregoing diagnosis and treatment procedures has been relatively limited. Other known uses for one such dye, ICG, are limited to diagnostic procedures, such as determining cardiac output, hepatic function and liver blood flow.

Accordingly, a need exists for methods of diagnosing and treating ocular vascular abnormalities, e.g., CNV, that overcome the aforementioned problems inherent in known methods of fluorescent dye angiography and photocoagulation. Further, and in view of the successful use of fluorescent dyes as diagnostics for certain limited conditions, i.e., ophthalmic angiograms, hepatic function and liver blood flow and cardiac output, there remain questions as to whether the use of these dyes can successfully be expanded into the diagnosis and/or treatment of other conditions and disorders.

SUMMARY OF THE INVENTION

The present invention meets the foregoing and other needs in a variety of ways. In a first aspect, the present invention provides a method for enhancing the clarity of fluorescent dye angiograms using relatively high dye concentrations, leading to more accurate targeting of vessels during treatment. In a second aspect, the present invention provides a method that allows blood vessels feeding various types of abnormalities to be more readily identified, and thereafter treated. Several other aspects of the present invention provide new methods of diagnosis and treating abnormalities and conditions using fluorescent dyes. All of the inventive aspects may be used on animals, e.g., humans, dogs, cats, but are preferably used in connection with the diagnosis and treatment of human subjects.

In particular, the present invention is able to provide angiograms of enhanced clarity by administering a plurality of relatively small boluses at relatively high dye concentrations to an animal undergoing an angiographic procedure. In particular, the method includes introducing boluses of about 0.1 ml to about 1.0 ml of a liquid composition at spaced time intervals into the animal to at least partially fill the blood vessels with the composition, wherein the liquid composition comprises a relatively high fluorescent dye and a carrier. For example, when using ICG, the dye concentration would be at least about 30 mg/ml, preferably at least about 40 mg/ml and most preferably at least about 50 mg/ml. Light energy of a type and in an amount sufficient to cause the dye in each bolus to fluoresce as the dye flows through the blood vessels is then applied, and angiographic images obtained.

Another aspect of the present invention provides a method for determining the direction of blood flow within a vessel. This may allow a physician to more readily determine whether a particular vessel is feeding an abnormality, indicating that it should be treated. The method includes at least the steps of administering a liquid composition comprising a fluorescent dye and a carrier into the animal to at least partially fill the blood vessel with the composition. Energy of a type and in an amount sufficient to cause the dye in the blood vessel to fluoresce is then applied. Subsequently, energy of a type and in an amount in excess of that required to cause the dye to fluoresce is applied to a portion of the fluorescing dye passing through the blood vessel to cause that portion of the fluorescing dye to stop fluorescing. A series of angiographs of both the fluorescing dye, and of the subsequent non-fluorescing portion thereof (also referred to as the "bleached" dye portion), are obtained, and those angiograms are compared to determine the direction of relative movement of the bleached dye. The direction of relative movement of the bleached dye portion indicates the direction of relative movement of the blood flow in the blood vessel.

Other aspects of the present invention involve new indications for fluorescent dyes. For example, one indication permits a physician to locate a tumor in or adjacent to the wall of a body cavity of an animal. This method includes administering a liquid composition comprising a fluorescent dye and a carrier into the animal to at least partially fill the blood vessels of the body cavity with the composition; applying energy of a type and in an amount sufficient to cause the dye to fluoresce as the dye flows through the blood vessels of the body c obtaining at least one angiographic image of the fluorescing dye as the dye flows through the blood vessels of the body cavity; and analyzing the angiographic image obtained in the prior step to determine whether a tumor is present in or adjacent to the wall of the body cavity. Related methods for diagnosing other types of lesions, e.g., ruptured blood vessels, abnormal vasculature, are also provided.

In other important aspects, the present invention provides methods for treating the aforementioned conditions. One exemplary method reduces the blood flow through a vessel that carries blood into a tumor of an animal. This method comprises administering a liquid composition comprising a fluorescent dye and a carrier into the animal to at least partially fill a blood vessel that carries blood into a tumor with the composition, and applying energy to the blood vessel of a type and in an amount sufficient to excite the dye in the blood vessel, thereby increasing the temperature of any liquid adjacent the dye, the increase in temperature causing the blood within the vessel to coagulate relatively quickly, thereby reducing (and preferably halting completely) the rate of blood flow through that vessel into the tumor.

Other related aspects of the present invention include methods for reducing or eliminating tumors. These methods are preferably used after the tumors have been located using fluorescent dye angiography, the latter providing a means for precisely locating a tumor in a subject. Once the precise location of a tumor is determined, methods including dye-enhanced photocoagulation, direct injection of chemotherapeutic and/or anti-angiogenesis agents into the tumor, conventional application of radiation, and surgical removal of the tumor, are expected to be effective against the tumor when used either alone or in combination. These methods have the advantage of lessening patient trauma because the treatment can be closely focused on the tumor alone as opposed to the tumor and other healthy body tissue, and may be used in combination in a single treatment session. For example, a single session can include dye-enhanced photocoagulation of those vessels feeding blood into the tumor using an endoscope, followed by injection of chemotherapeutic and anti-angiogenesis agents via the endoscope directly into the tumor itself (as opposed to conventional IV administration).

The various aspects of the present invention will be more clearly understood upon reference to the following preferred embodiments.

DETAILED DESCRIPTION OF THE PREFERRED EMBODIMENTS

Turning initially to the issues associated with angiogram clarity, a first aspect of the present invention provides a method for enhancing the resolution of angiograms. This enhancement is provided by the introduction of a plurality of relatively small, yet highly dye-concentrated, boluses of a fluorescent dye composition into an animal, and subsequently obtaining angiograms as the composition passes through the vasculature of interest. The use of this method provides for a greater degree of fluorescence in the composition, and hence greater resolution in the associated angiogram, as compared to angiograms obtained using a composition having a conventional dye concentration.

Prior to the discovery of the present invention, there was no recognized need in any diagnostic or therapeutic procedure for using a fluorescent dye at a relatively high concentration. For example, one example of a suitable dye, ICG, has been marketed for years for use in angiography. The present package insert for IC-GREEN™ (ICG, manufactured by Akorn, Inc., Decatur, Ill.) suggests an optimal concentration of 20 mg ICG/ml for angiography (at 2 ml, providing a total ICG dose of 40 mg), depending upon the imaging equipment and technique used.

In contrast, this aspect of the invention includes introducing boluses of a liquid composition comprising a fluorescent dye at a concentration that is higher than that previously used. This concentration should be at least about 1.5 times (e.g., about 30 mg/ml for ICG), preferably at least about 2 times (e.g., about 40 mg/ml for ICG) and most preferably about 2.5 times (e.g., at least about 50 mg/ml for ICG) the highest known angiographic diagnostic concentration. The boluses are advantageously small in volume, about 0.1 ml to about 1.0 ml, and may be of the same or different volume. The boluses are introduced at spaced time intervals into an animal to at least partially fill the blood vessels of interest with the composition. After this administration, light energy of a type and in an amount sufficient to cause the dye to fluoresce as the dye flows through the blood vessels is applied, in accordance with procedures known in the art, and angiographic images are obtained. The images obtained provide higher levels of resolution than those obtained using conventional dye (e.g., ICG) compositions.

While not being bound to any particular theory, it is believed that the enhancement of resolution is due to the greater number of dye molecules present in a given wave front transiting a blood vessel, and a recognition that CCD cameras (typically used to obtain angiographic images) generate relatively high signal-to-noise ratios. With the relatively greater number of dye molecules being present in a particular dye "wave front," a greater the number of photons are generated by the dye upon exposure to radiation, providing better image quality even when the relatively high signal-to-noise ratio CCD cameras are used.

The total quantity of the liquid composition administered through a plurality of boluses (or as a single bolus, if desired) should be sufficient to permit readable angiographic images to be obtained and analyzed when using a CCD camera. This quantity may equal that administered using conventional formulations, but is advantageously greater, e.g., at least about 1.5 times the amount of dye administered using conventional formulations. More advantageously, at least twice that amount, preferably at least three times that amount, and most preferably, at least five times the amount of conventional formulations is administered. Optionally, after the administration of each bolus, a saline flush can be administered to aid the circulation of the liquid composition throughout the blood vessels of interest.

The dyes useful in the present invention should be able to fluoresce in the presence of radiation of a certain wavelength, and to permit angiographic images of blood vessels of higher quality to be obtained as compared to angiograms obtained using conventional dye concentrations. Preferably, the dyes should also be able to generate thermal energy when exposed to radiation. The dyes should therefore be selected to at least permit diagnostic procedures, while preferred dyes function for both diagnostic and treatment procedures.

Treatment methods using dye-enhanced photocoagulation discussed herein comprise applying radiation of a certain wavelength (based upon the dye used) on a portion of an undesirable dye-carrying blood vessel. The radiation wavelength is selected to "excite" the dye; the absorption of such radiation by the dye causes the temperature of the dye to increase. As the correlation between radiation wavelength and increase in dye temperature is well known to those skilled in the art, this data will not be repeated herein. As the dye temperature increases, the temperature of the surrounding blood and vessel tissue increase. This increase in temperature hastens the rate at which blood clots in and adjacent that portion of the vessel onto which the radiation is applied. This clotting, in turn, leads to partial, or preferably complete, obstruction of the vessel in or adjacent the portion of the vessel onto which the radiation was applied.

The dye-containing composition used in this and the other treatment methods disclosed herein may vary widely. One limit on the dye concentration is that sufficient dye should be present in composition, and more importantly the targeted vessel, to permit at least partial obstruction of the target vessel by the dye-enhanced photocoagulation methods discussed herein. Further, the novel diagnostic methods disclosed in the following paragraphs may also use a wide range of dye concentrations, with the limitation that sufficient dye should be present in the composition (and targeted vessels) to permit the angiograms taken in conjunction with those methods to be analyzed.

One method of determining the degree of vessel obstruction is by analyzing angiograms taken after treatment is completed, and after the dye has left the treated vessel. For example, if the treatment results in total obstruction of a CNV feeder vessel, an angiogram of the downstream portion of the vessel, e.g., the CNV itself, will not reveal any dye fluorescence. Partial obstruction should reveal a lower degree of fluorescence.

A number of fluorescent dyes are known that are acceptable for use in the composition of the various inventive methods described herein. Exemplary dyes include fluorescein, rose bengal, ICG and analogue members of the tricarbocyanine dyes, and any other dye which meets the criteria described herein for diagnosis and/or treatment procedures. The preferred fluorescent dye is ICG because it is readily available, has long been approved for administration to humans for ophthalmic angiography and other unrelated indications, and is suitable for both diagnosis and treatment procedures. As the peak absorption and emission of ICG lies in the range of 800–850 nm, a light source emitting such wavelengths should be used when obtaining angiographic images during diagnosis, as well as during any subsequent treatment procedure.

The dye compositions may further include a pharmaceutically-acceptable carrier. The carrier enhances the administration of the fluorescent dye to a patient, the latter being either intravenously or by other suitable means. The choice of carrier will be determine in part by the particular fluorescent dye used, as well as by the particular route of administration of the liquid composition. The carrier should be compatible with both the fluorescent dye and the tissues and organs of the subject that come into contact with the liquid composition. Moreover, the carrier should not interfere with the energy applied or angiographic images obtained following administration.

Illustrative of suitable carriers include water, saline, alcohols, red blood cells (RBC), glycerin, polyethylene glycol, propylene glycol, polysorbate 80, Tweens, liposomes, amino acids, lecithin, dodecyl sulfate, lauryl sulfate, phospholipid, Cremophor, desoxycholate, soybean oil, vegetable oil, safflower oil, sesame oil, peanut oil, cottonseed oil, sorbitol, acacia, aluminum monstearate, polyoxyethylated fatty acids, povidone and mixtures thereof. Advantageously, the carrier is water. Preferably, however, the composition will include components that increase the degree of dye fluorescence, e.g., alcohols such as ethanol and surfactants such as the Tweens. Optional components that may be present in the composition include tonicity and/or pH adjusters, e.g., NaOH, HCl, tribuffer phosphate, tris buffer and the like. In addition, the composition may include thrombin or other known blood clotting compounds that would function to further enhance blood clotting during and after treatment.

The fluorescent dye composition may initially be provided as a lyophilizate for reconstitution before use, or as a pre-mix, in a vial or syringe.

As mentioned above, and in a related aspect of the present invention, RBCs may be used as a carrier for the fluorescent dye. This technique is referred to herein as RBC doping. The RBC as a carrier has advantages in that it is a normal constituent of circulating blood and, despite the relative large volume (and hence large dye-carrying capacity) of each RBC, RBCs can nevertheless readily move throughout the circulatory system—deforming to enable movement through even the small diameter capillaries. Further, and while not desiring to be bound to any particular theory, the use of doped RBCs provides additional advantages pertaining to clot formation. In particular, the size of clot formed during the treatment methods described herein depends upon the amount of dye present at the vessel treatment site, the amount of radiation energy delivered thereto and the distribution of the dye molecules associated with the RBCs. The greater the number of dye molecules associated with the RBCs, the more sizable the clot will be when exposed to appropriate radiation during the treatment phase. Of course, if the clot is large enough, vessel closure will be permanent. However, if smaller, as is often the case using conventional treatment methods, the clot will resolve, requiring additional treatment. The doping of dye in RBCs reduces the variability in clot formation because it increases the fraction of dye molecules associated with RBCs at the treatment site, thereby increasing the probability that a sizable clot is formed during treatment.

The object of the procedure is to remove the content of the RBCs, and then refill the RBCs with hemoglobin and dye, e.g., ICG, and, if desired, other clot potentiating compounds, e.g., fibrin. When the use of RBC doping is indicated, the following exemplary procedure may be followed to provide the doped composition for use in the various inventive methods described herein. Preferably, a small amount of the subject's blood is withdrawn (about 10–15 ml), although any compatible blood may be used, and is centrifuged to permit removal of the serum. The remaining RBCs are washed in normal PBS to remove proteins from the RBC surface. The washed RBCs are placed in a cooled hemolizing solution, and incubated therein for about 5 min. The pH of the solution is readjusted to 7.2, and ICG is added. The solution is again incubated at 37° C. for about 45–60 min. If desired, other compounds that assist in clotting, e.g., fibrin, may be added at this stage. The solution is then centrifuged at about 500 g for about 6 min, and the supernatant is removed. The resulting cells are washed several times to remove ICG not associated with the RBCs. ICG-doped RBCs are provided, which may then be injected into a subject as a bolus for diagnostic purposes, and preferably for purposes of effecting treatment, in accordance with the methods described herein. When used for treatment, uptake of the radiation should be potentiated to ensure that a relatively high number of RBCs are exploded at the target site in the vessel.

Liposomes may also be used in connection with the present invention as a carrier for the dye. As technology providing for the formation of liposomes is well known, such will not be repeated herein. However, the following are illustrative of components that are expected to provide suitable dye-carrying liposomes: cholesterol, stearic acid, egg phosphotidyl choline, and stearyl amine.

It should be appreciated that in connection with the various novel indications (e.g., diagnosis and treatment of lesions, tumors and ruptured vessels, among others) and novel carriers (e.g., liposomes and RBCs) disclosed herein, the concentration of the fluorescent dye present in the liquid composition, and the injection of relatively small boluses of the composition, is not critical. At a minimum, however, the amount of fluorescent dye used in those methods must be present in the composition at a concentration that permits the dye to fluoresce when radiation at appropriate wavelength is applied, providing useful angiographic images. The same standard is applicable to the treatment methods; sufficient dye should be utilized to enable the desired treatment. This information may be readily determined by those skilled in the art, and should be at least that concentration currently accepted for use in ophthalmic angiography, e.g., for diagnosis, 2 ml of a 20 mg/ml ICG solution (IC-GREEN™). Of course, the relatively higher dye concentrations described previously herein may advantageously be used in any of these diagnostic and treatment methods.

Any suitable source of radiation that causes the particular dye to fluoresce as it flows through the vessels of interest may be used in the present methods. The type and amount of energy applied to the blood vessels of interest must be sufficient to cause the fluorescent dye present in these blood vessels to fluoresce. The energy applied must be within the limits of the maximum flux density or irradiance which can be applied to the blood vessels of interest within a particular time span without causing excessive damage to the normal surrounding tissue. The longer the duration of exposure to the energy source, the lower the allowable level of irradiance. The particular energy source and amount of energy applied will depend upon the type of fluorescent dye administered to the subject.

The radiation used in the methods described herein is preferably applied using a laser, and, most preferably, using a pulsed laser. The pulsing of the laser provides the advantage of generating a greater number of photons for image formation in the shortest time interval. Various devices, preferably fundus cameras, can be adapted for providing an appropriate level and type of radiation in accordance with the teachings provided herein. The latter include, for example, those described in U.S. Pat. Nos. 5,279,298, 5,394,199 and 5,400,791. Preferably, a fundus camera having two sources of radiation (e.g., lasers) is provided. Using such a camera, one laser can be used to irradiate the general area of interest so any vessels requiring treatment can be identified, while the second laser can be used almost immediately upon identification of the vessel to be treated to hasten the coagulation of the blood therein, i.e., dye-enhanced photo-coagulation. The ability to aim the treatment laser using the identical view used to obtain the angiograns is a significant advantage. Further, the ability to complete the diagnosis and treatment steps within minutes, e.g., advantageously in less than about 30 and preferably less than about 15 minutes, lessens patient trauma and increases overall treatment efficiency.

The present invention further provides novel methods for visualizing blood vessels at locations other than in the eye. Generally, the method now permits angiograms of blood vessels and other abnormalities associated with blood vessels to be obtained at any location in an animal in which readable angiographic images can be obtained. For example, the interior wall of the bladder, stomach, colon may be explored, as well as the exterior walls of those organs. This permits the diagnosis and treatment of abnormal blood vessels, such as aneurysms, ruptured blood vessels, e.g., those associated with a stroke or physical trauma, as well as the diagnosis and treatment of tumors and other such lesions associated with those and other body cavity tissues.

An endoscope may advantageously be used to obtain the previously mentioned angiograms. The endoscope would be inserted into the body and positioned adjacent the area of interest. A first instrument would be used with the endoscope to provide radiation at an appropriate wavelength, e.g., a laser optic cable, to cause the dye within the subject vessels to fluoresce so an angiogram can be obtained. Similarly, a second instrument would be used with the endoscope that would permit an angiographic image of the fluorescing dye within the vessels to be obtained. For example, an optical device connected to a CCD camera, such as those used to perform a colonoscopy and other invasive procedures to permit a physician to view the interior of a body cavity, presently exists, and such technology may be readily adapted for use in conjunction with the endoscopic procedures of the present invention.

After injection of the dye composition, and flow of the composition through the region expected to be afflicted, an angiogram would then be obtained using what are referred to herein as the first and second instruments, and any abnormal vessels detected thereby treated, using the procedures described previously for diagnosis and treatment.

In the context of the present invention, the term "body cavity" includes any cavity that permits the introduction of an endoscope or other instrument that permits the use of appropriate radiation and imaging equipment required to obtain an angiogram. Illustrative of body tissues associated with suitable cavities are the eye, lung, gastrointestinal tract, bladder, pancreas, gall bladder, sinus, heart, cervix, brain, ovaries, prostate, stomach and skin.

Treatment is preferably effected by applying radiation upstream of the lesion, e.g., upstream of the ruptured blood vessel, the vessel feeding the tumor, or adjacent and upstream of the abnormal blood vessels, after administration of the dye composition. The temperature of any liquid adjacent the dye receiving the radiation is raised, and the blood clotting is hastened, thereby reducing, e.g., partially or completely preventing, the flow of blood through the vessel. Varicose veins may also be treated using the aforementioned treatment methods.

When the treatment of a tumor, advantageously a solid tumor, is undertaken, the method of the present invention is preferably used in combination with other treatment agents. For example, therapeutically-effective amounts of chemotherapeutic agents, such as cisplatin, carboplatin, doxorubicin, paclitaxel, taxotere, methotrexate, fluorouracil, camptothecin, cyclophosphamide and mixtures thereof, may be administered, as well as therapeutically-effective amounts of anti-angiogenesis agents, either alone or in combination, may be administered. The identity of suitable anti-tumor and anti-angiogenesis agents and associated dosage regimens are well known, and as such will not be repeated herein. The timing of administration of these agents may occur at any time so long as the administration does not interfere with the treatment method of the present invention. Advantageously, however, the agents may be administered in combination with the dye-enhanced photocoagulation treatment methods described herein. For example, the agents can be administered immediately after dye-enhanced photocoagulation of tumor feeder vessels, and preferably are injected directly into the tumor. This provides several advantages including the reduction of trauma to the patient because multiple treatment agents are administered in a single procedure, the chemotherapeutic and anti-angiogenesis agents are delivered directly to the tumor thereby limiting the exposure of healthy tissue to these toxic agents (as would be the case using conventional IV administration), and conventional radiation can be narrowly focused on the tumor itself, as opposed to conventional methods that irradiate an area surrounding the tumor.

Conventional radiation treatment, mentioned previously, and surgical intervention, may also be used individually or in combination after the diagnostic methods of the present invention have been used, or alternatively in combination with the treatment methods of the present invention.

When diagnosis of the tumor is made in accordance with the angiogram methodology of the present invention, the location and boundaries of the tumor may be determined with a high degree of precision, without resort to the use of more harmful diagnostic procedures, e.g., X-rays. The precision provided by the present invention permits the treatment agents described previously to be more efficient because they are applied with a high degree of precision onto just the tumor itself, as compared to conventional methods, e.g., systemic administration of chemotherapeutic agents and application of radiation, which are applied over a more general area. This precise focus, in turn, lessens trauma to the subject by minimizing the side effects of these toxic agents.

In another embodiment, the present invention also provides a method for determining the direction of blood flow in a blood vessel of a patient. This method is of significance in identifying those arteries that are providing blood to a lesion, e.g., CNV, tumor or other blood vessel abnormality. Once these arteries are identified, the preferred dye-enhanced photocoagulation treatment described herein can be used to at least partially preclude, or preferably completely preclude, the flow of blood through the arteries. This would have the effect of "starving" the CNV, lesion, tumor or other abnormality, causing a reduction in size or complete elimination.

The method, which uses a technique referred to herein as "bleaching," comprises administering the aforesaid liquid dye composition to the subject to at least partially fill the blood vessels in the area to be examined with the composition. Thereafter, radiation of a type and in an amount sufficient to cause the dye in the blood vessel to fluoresce is applied. After the dye begins to fluoresce, radiation of a type and in an amount in excess of that required to cause the dye to fluoresce is applied to a portion of the fluorescing dye passing through the blood vessel to cause that portion of the fluorescing dye to stop fluorescing, i.e., a portion of the fluorescing dye is "bleached." Beginning at this point in time, or optionally before, angiograms are obtained at selected time intervals, and these angiograms are compared to determine the direction of relative movement of that portion of the dye no longer fluorescing, i.e., the "bleached" dye. This comparison can be made by reviewing the angiograms taken using a CCD video device, wherein the relative movement of the bleached portion of the dye indicates the direction of relative movement of the blood flow in the blood vessel.

Where appropriate, and unless otherwise indicated, the fluorescent dye, carrier, liquid composition characteristics, administration of the liquid composition, application of radiation for diagnosis and treatment, and obtaining angiographic images described in connection with the method of visualizing and treating blood vessels using relatively high dye concentrations are equally applicable to the foregoing novel methods for visualizing arteries that are providing blood to any type of lesion, e.g., CNV, tumor or other abnormality associated with blood vessels, and treating those blood vessels, as well as determining blood flow direction.

All of the references cited herein, including patents, patent applications, and publications, are hereby incorporated in their entireties by reference. Further, and unless otherwise indicated, references to a single component or step should be construed as also including more than one component or step, i.e., at least one.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for visualizing blood vessels located within a preselected area in an animal comprising
   (a) administering a plurality of boluses of about 0.1 ml to about 1.0 ml of a liquid composition at spaced time intervals into the animal, wherein the liquid composition comprises a fluorescent dye and a carrier;
   (b) endoscopically applying energy of a type and in an amount sufficient to cause the dye in each bolus to fluoresce as the dye flows through the blood vessels located within the preselected area; and
   (c) obtaining a plurality of angiographic images of the fluorescing dye in each bolus using a video camera as the dye enters the blood vessels located within the preselected area and continues to flow through the blood vessels.

2. The method according to claim 1, wherein the blood vessels are in tissue which defines a body cavity.

3. The method according to claim 2, wherein the tissue is located in the eye, lung, gastrointestinal tract, bladder, pancreas, gall bladder, sinus, heart, cervix, brain, ovary, prostate, stomach or skin.

4. The method of claim 1, wherein the energy is applied in a plurality of discrete pulses.

5. The method of claim 1, wherein the carrier comprises at least one liposome having dye encapsulated therein.

6. The method of claim 1, wherein the carrier comprises at least one red blood cell having dye encapsulated therein.

7. The method of claim 1, wherein the dye consists essentially of indocyanine green and is present at a concentration of at least about 20 mg/ml.

8. A method for visualizing blood vessels located within a preselected area in an animal comprising (a) administering a liquid composition, wherein the liquid composition comprises a fluorescent dye encapsulated within red blood cells;

(b) applying energy of a type and in an amount sufficient to cause the dye to fluoresce as the dye flows through the blood vessels located within the preselected area; and (c) obtaining at least one angiographic image of the fluorescing dye as the liquid composition flows through the blood vessels.

9. The method of claim 8, wherein in step (c), a plurality of angiographic images of the fluorescing dye is obtained for each bolus using a video camera as the dye enters the blood vessels located within the preselected area and continues to flow through the blood vessels.

10. The method of claim 9, wherein the dye consists essentially of indocyanine green and is present at a concentration of at least about 20 mg/ml.

11. The method of claim 10, wherein the indocyanine dye is present at a concentration of at least about 30 mg/ml.

12. A method for determining the direction of blood flow in a blood vessel of an animal comprising (a) administering a liquid composition comprising a fluorescent dye and a carrier into the animal to at least partially fill the blood vessel with the composition;

(b) applying energy of a type and in an amount sufficient to cause the dye in the blood vessel to fluoresce;

(c) applying energy of a type and in an amount in excess of that required to cause the dye to fluoresce to a portion of the fluorescing dye passing through the blood vessel to cause that portion of the fluorescing dye to stop fluorescing;

(d) obtaining a plurality of angiographic images of the fluorescent dye subsequent to step (c); and (e) comparing the angiographic images obtained in step (d) to determine the direction of relative movement of that portion of the dye that no longer fluoresces because of the application of energy during step (c), and thereby the direction of relative movement of the blood flow in the blood vessel.

13. The method according to claim 12, wherein the blood vessel is in tissue which defines a body cavity.

14. The method according to claim 13, wherein the tissue is located in the eye, lung, gastrointestinal tract, bladder, pancreas, gall bladder, sinus, heart, cervix, brain, ovary, prostate, stomach or skin.

15. The method of claim 12, wherein the carrier comprises at least one liposome having dye encapsulated therein.

16. The method of claim 12, wherein the carrier comprises at least one red blood cell having dye encapsulated therein.

17. A method for locating a tumor in or adjacent to tissue defining a body cavity of an animal comprising (a) administering a liquid composition comprising a fluorescent dye and a carrier into the animal to at least partially fill the blood vessels of the body cavity tissue with the composition;

(b) applying energy of a type and in an amount sufficient to cause the dye to fluoresce as the dye flows through the blood vessels of the body cavity tissue;

(c) obtaining at least one angiographic image of the fluorescing dye as the dye flows through the blood vessels of the body cavity tissue; and (d) analyzing the angiographic image obtained in step (c) to determine whether a tumor is present in or adjacent to the body cavity tissue, wherein the body cavity tissue is located in the lung, gastrointestinal tract, bladder, pancreas, gall bladder, sinus, heart, cervix, brain, ovary, prostate, stomach or skin, wherein the liquid composition is administered in a plurality of boluses at spaced time intervals, and wherein the concentration of dye in each bolus is relatively high.

18. The method of claim 17, wherein each bolus includes from about 0.1 ml to about 1.0 ml of the liquid composition.

19. The method of claim 17, wherein the energy is applied in a series of discrete pulses.

20. The method of claim 17, wherein the energy is applied using an endoscope.

21. The method of claim 17, wherein the carrier comprises at least one liposome having dye encapsulated therein.

22. The method of claim 17, wherein the carrier comprises at least one red blood cell having dye encapsulated therein.

23. The method of claim 17, wherein the dye consists essentially of indocyanine green and is present at a concentration of at least about 20 mg/ml.

24. The method of claim 23, wherein the indocyanine dye is present at a concentration of at least about 30 mg/ml.

25. A method for diagnosing and treating a lesion in an animal wherein a blood vessel within a preselected area of vasculature feeds blood into the lesion comprising (a) administering a plurality of boluses of about 0.1 ml to about 1.0 ml of a liquid composition at spaced time intervals into the animal, wherein the liquid composition comprises a fluorescent dye at a relatively high concentration and a carrier;

(b) endoscopically applying energy of a type and in an amount sufficient to cause the dye in each bolus to fluoresce as the dye flows through the preselected vasculature;

(c) obtaining a plurality of angiographic images of the fluorescing dye in each bolus using a video camera as the dye enters the preselected vasculature and continues to flow through the vasculature;

(d) analyzing the angiographic images obtained in step (c) to determine the presence of a lesion and a blood vessel feeding blood into the lesion; and (e) applying energy to the blood vessel feeding blood into the lesion of a type and in an amount sufficient to excite the dye in the blood vessel and reduce the rate of rate of blood flow through the blood vessel.

26. The method of claim 25, wherein in step (b) the energy is applied in a series of discrete pulses.

27. The method according to claim 25, wherein the blood vessels feeding the lesion are in tissue which defines a body cavity.

28. The method according to claim 27, wherein the tissue is located in the eye, lung, gastrointestinal tract, bladder, pancreas, gall bladder, sinus, heart, cervix, brain, ovary, prostate, stomach or skin.

29. The method of claim 25, wherein the carrier comprises at least one liposome having dye encapsulated therein.

30. The method of claim 25, wherein the carrier comprises at least one red blood cell having dye encapsulated therein.

31. The method of claim 25, wherein the dye consists essentially of indocyanine green and is present at a concentration of at least about 20 mg/ml.

32. The method of claim 31, wherein the indocyanine dye is present at a concentration of at least about 30 mg/ml.

33. A method for diagnosing and treating an abnormal blood vessel located within a preselected area in an animal comprising (a) administering a plurality of boluses of about 0.1 ml to about 1.0 ml of a liquid composition at spaced time intervals into the animal, wherein the liquid composition comprises a fluorescent dye at a relatively high concentration and a carrier;

(b) endoscopically applying energy of a type and in an amount sufficient to cause the dye in each bolus to fluoresce as the dye flows through the preselected area of blood vessels;

(c) obtaining a plurality of angiographic images of the fluorescing dye in each bolus using a video camera as the dye enters the preselected vasculature and continues to flow through the vasculature;

(d) analyzing the angiographic images obtained in step (c) to determine the presence of an abnormal blood vessel; and e) applying energy to the abnormal blood vessel of a type and in an amount sufficient to excite the dye in the abnormal blood vessel and reduce the rate of blood flow through the abnormal blood vessel.

34. The method of claim 33, wherein in step (b) the energy is applied in a series of discrete pulses.

35. The method according to claim 33, wherein the blood vessels are in tissue that defines a body cavity.

36. The method according to claim 35, wherein the tissue is located in the eye, lung, gastrointestinal tract, bladder, pancreas, gall bladder, sinus, heart, cervix, brain, ovary, prostate, stomach or skin.

37. The method of claim 33, wherein the carrier comprises at least one liposome having dye encapsulated therein.

38. The method of claim 33, wherein the carrier comprises at least one red blood cell having dye encapsulated therein.

39. The method of claim 33, wherein the dye consists essentially of indocyanine green and is present at a concentration of at least about 20 mg/ml.

40. The method of claim 39, wherein the indocyanine dye is present at a concentration of at least about 30 mg/ml.

41. A method for reducing the rate of blood flow through a vessel that carries blood into a tumor associated with a body cavity of an animal comprising (a) administering intravenously a liquid composition comprising a fluorescent dye and a carrier into the animal to at least partially fill a blood vessel that carries blood into a tumor associated with a body cavity with the composition;

(b) endoscopically applying energy to the blood vessel of a type and in an amount sufficient to excite the dye in the blood vessel and reduce the rate of blood flow through the vessel carrying blood into the tumor.

42. The method according to claim 41, wherein the tumor is located in the tissue of an eye, lung, gastrointestinal tract, bladder, pancreas, gall bladder, sinus, heart, cervix, brain, ovary, prostate, stomach or skin.

43. The method of claim 41, wherein the carrier comprises at least one liposome having dye encapsulated therein.

44. The method of claim 41, wherein the carrier comprises at least one red blood cell having dye encapsulated therein.

45. The method of claim 41, further comprising administering an effective amount of a chemotherapeutic agent.

46. The method of claim 45, further comprising administering an effective amount of an anti-angiogenesis agent.

47. The method of claim 46, further comprising administering radiation in an amount effective to reduce the size of the tumor.

48. The method of claim 41, further comprising administering an effective amount of an anti-angiogenesis agent.

49. The method of claim 41, further comprising administering radiation in an amount effective to reduce the size of the tumor.

50. A method for diagnosing a ruptured blood vessel located within a preselected area of vasculature in an animal comprising (a) administering a liquid composition comprising a fluorescent dye and a carrier into the animal;

(b) endoscopically applying energy of a type and in an amount sufficient to cause the dye to fluoresce as the dye flows through the preselected area of vasculature of the animal;

(c) obtaining a plurality of angiographic images of the fluorescing dye using a video camera as the dye enters the preselected vasculature and continues to flow through the vasculature; and (d) analyzing the angiographic image obtained in step (c) to determine whether a ruptured blood vessel is present in the animal.

51. The method of claim 50, wherein in step (b) the energy is applied in a series of discrete pulses.

52. The method according to claim 50, wherein the ruptured blood vessel is in an eye, lung, gastrointestinal tract, bladder, pancreas, gall bladder, sinus, heart, cervix, brain, ovary, prostate, stomach or skin.

53. The method of claim 50, wherein the carrier comprises at least one liposome having dye encapsulated therein.

54. The method of claim 50, wherein the carrier comprises at least one red blood cell having dye encapsulated therein.

55. A method of for reducing the blood flow through a rupture in a blood vessel in an animal comprising (a) administering intravenously a liquid composition comprising a fluorescent dye consisting essentially of indocyanine green and a carrier into the animal to at least partially fill the ruptured blood vessel with the composition; and (b) endoscopically applying energy to the blood vessel upstream of the rupture of a type and in an amount sufficient to excite the indocyanine green dye in the blood vessel and reduce the rate of blood flow through the rupture.

56. The method according to claim 55, wherein the ruptured blood vessel is located in the tissue of an eye, lung, gastrointestinal tract, bladder, pancreas, gall bladder, sinus, heart, cervix, brain, ovary, prostate, stomach or skin.

57. The method of claim 55, wherein the carrier comprises at least one liposome having dye encapsulated therein.

58. The method of claim 55, wherein the carrier comprises at least one red blood cell having dye encapsulated therein.

59. A method for visualizing blood vessels in an animal using an endoscope comprising (a) administering intravenously a liquid composition comprising a fluorescent dye and a carrier to the animal;

(b) inserting an endoscope into the animal in a location adjacent the blood vessels desired to be visualized, wherein the endoscope includes a first instrument capable of emitting energy of a type and in an amount sufficient to cause the dye to fluoresce as the dye flows through the blood vessels and a second instrument comprising a video camera capable of enabling angiographic images of the blood vessels to be obtained;

(c) activating the first instrument to apply energy of a type and in an amount sufficient to cause the dye to fluoresce as the dye flows through the blood vessels; and (d) activating the second instrument to obtain a plurality of angiographic images of the fluorescing dye through the endoscope as the dye enters and flows through the blood vessels.

60. A method for reducing the rate of blood flow through a vessel using an endoscope comprising
    (a) administering parenterally a liquid composition comprising a fluorescent dye and a carrier into the animal;
    (b) inserting the endoscope in a location adjacent the blood vessel desired to be visualized, wherein the endoscope includes an instrument capable of emitting energy of a type and in an amount sufficient to excite the dye in the blood vessel and reduce the rate of blood flow through the vessel;
    (c) activating the instrument to apply energy of a type and in an amount sufficient to excite the dye in the blood vessel and reduce the rate of blood flow through the vessel.

61. A method for locating and treating a tumor in or adjacent to tissue defining a body cavity of an animal comprising
    (a) administering intravenously a liquid composition comprising a fluorescent dye and a carrier into the animal;
    (b) applying energy of a type and in an amount sufficient to cause the dye to fluoresce as the dye flows through the blood vessels of the body cavity tissue;
    (c) obtaining at least one angiographic image of the fluorescing dye as the dye flows through the blood vessels of the body cavity tissue;
    (d) analyzing the angiographic image obtained in step (c) to determine whether a tumor is present in or adjacent to the body cavity tissue and the location of any blood vessel that feeds blood into the tumor; and
    (e) applying to any blood vessel located in step (d) that feeds blood into the tumor energy of a type and in an amount sufficient to excite the dye in the blood vessel and reduce the rate of blood flow through the vessel carrying blood into the tumor,
    wherein the liquid composition is administered in a plurality of boluses at spaced time intervals, and the dye concentration in each bolus is relatively high.

62. The method of claim 61, further comprising administering an effective amount of a chemotherapeutic agent.

63. The method of claim 62, further comprising administering an effective amount of an anti-angiogenesis agent.

64. The method of claim 63, further comprising administering radiation in an amount effective to reduce the size of the tumor.

65. The method of claim 62, wherein the administration is effected by injecting the chemotherapeutic agent directly into the tumor.

66. The method of claim 61, further comprising administering an effective amount of an anti-angiogenesis agent.

67. The method of claim 66, wherein the administration is effected by injecting the anti-angiogenesis agent directly into the tumor.

68. The method of claim 61, further comprising administering radiation in an amount effective to reduce the size of the tumor.

69. A method for locating a tumor in or adjacent to tissue defining a body cavity of an animal comprising
    (a) administering about 0.1 ml to about 1.0 ml of a liquid composition comprising a fluorescent dye and a carrier into the animal to at least partially fill the blood vessels of the body cavity tissue with the composition;
    (b) applying energy of a type and in an amount sufficient to cause the dye to fluoresce as the dye flows through the blood vessels of the body cavity tissue;
    (c) obtaining at least one angiographic image of the fluorescing dye as the dye flows through the blood vessels of the body cavity tissue; and
    (d) analyzing the angiographic image obtained in step (c) to determine whether a tumor is present in or adjacent to the body cavity tissue,
    wherein the body cavity tissue is located in the lung, gastrointestinal tract, bladder, pancreas, gall bladder, sinus, heart, cervix, brain, ovary, prostate, stomach or skin.

70. The method of claim 69, wherein the dye consists essentially of indocyanine green and is present in the liquid composition at a concentration of at least about 20 mg/ml.

71. A method for visualizing blood vessels located within a preselected area in an animal comprising
    (a) administering a plurality of boluses comprised of about 0.1 ml to about 1.0 ml of a liquid composition at spaced time intervals into the animal, wherein the liquid composition comprises a fluorescent dye and a carrier;
    (b) applying energy of a type and in an amount sufficient to cause the dye in each bolus to fluoresce as the dye flows through the blood vessels located within the preselected area; and
    (c) obtaining a plurality of angiographic images of the fluorescing dye in each bolus using a video camera as the dye enters the blood vessels located within the preselected area and continues to flow through the blood vessels,
    wherein the fluorescent dye consists essentially of indocyanine green and is present in the liquid composition at a concentration of at least about 20 mg/ml.

72. The method of claim 71, wherein the indocyanine dye is present at a concentration of at least about 30 mg/ml.

73. A method for locating a tumor in or adjacent to tissue defining a body cavity of an animal comprising
    (a) administering a liquid composition comprising a fluorescent dye and a carrier into the animal to at least partially fill the blood vessels of the body cavity tissue with the composition;
    (b) applying energy of a type and in an amount sufficient to cause the dye to fluoresce as the dye flows through the blood vessels of the body cavity tissue;
    (c) obtaining a plurality of angiographic images of the fluorescing dye using a video camera as the dye enters and flows through the blood vessels of the body cavity tissue; and
    (d) analyzing the angiographic image obtained in step (c) to determine whether a tumor is present in or adjacent to the body cavity tissue,
    wherein the body cavity tissue is located in the lung, gastrointestinal tract, bladder, pancreas, gall bladder, sinus, heart, cervix, brain, ovary, prostate, stomach or skin.

74. A method for locating a tumor in or adjacent to tissue defining a body cavity of an animal comprising
    (a) administering a plurality of boluses of from about 0.1 ml to about 1.0 ml of a liquid composition comprising a fluorescent dye and a carrier into the animal to at least partially fill the blood vessels of the body cavity tissue with the composition;
    (b) applying energy of a type and in an amount sufficient to cause the dye to fluoresce as the dye flows through the blood vessels of the body cavity tissue;
    (c) obtaining angiographic images of the fluorescing dye using a video camera as the dye enters and flows through the blood vessels of the body cavity tissue; and (d) analyzing the angiographic image obtained in step (c) to determine whether a tumor is present in or adjacent to the body cavity tissue, wherein the body cavity tissue is located in the lung, gastrointestinal tract, bladder, pancreas, gall bladder, sinus, heart, cervix, brain, ovary, prostate, stomach or skin.

75. A method for diagnosing and treating a lesion in an animal wherein a blood vessel within a preselected area of vasculature feeds blood into the lesion comprising
    (a) administering a plurality of boluses of about 0.1 ml to about 1.0 ml of a liquid composition at spaced time intervals into the animal, wherein the liquid composition comprises a fluorescent dye consisting essentially of indocyanine green at a concentration of at least about 20 mg/ml of the liquid composition and a carrier;
    (b) applying energy of a type and in an amount sufficient to cause the dye in each bolus to fluoresce as the dye flows through the preselected vasculature;
    (c) obtaining a plurality of angiographic images of the fluorescing dye in each bolus using a video camera as the dye enters the preselected vasculature and continues to flow through the vasculature;
    (d) analyzing the angiographic images obtained in step (c) to determine the presence of a lesion and a blood vessel feeding blood into the lesion; and
    (e) applying energy to the blood vessel feeding blood into the lesion of a type and in an amount sufficient to excite the dye in the blood vessel and reduce the rate of rate of blood flow through the blood vessel.

76. A method for diagnosing and treating an abnormal blood vessel located within a preselected area in an animal comprising
    (a) administering a plurality of boluses of about 0.1 ml to about 1.0 ml of a liquid composition at spaced time intervals into the animal, wherein the liquid composition comprises a fluorescent dye consisting essentially of indocyanine green at a concentration of at least about 20 mg/ml of the liquid composition and a carrier;
    (b) applying energy of a type and in an amount sufficient to cause the dye in each bolus to fluoresce as the dye flows through the preselected area of blood vessels;
    (c) obtaining a plurality of angiographic images of the fluorescing dye in each bolus using a video camera as the dye enters the preselected vasculature and continues to flow through the vasculature;
    (d) analyzing the angiographic images obtained in step (c) to determine the presence of an abnormal blood vessel; and
    (e) applying energy to the abnormal blood vessel of a type and in an amount sufficient to excite the dye in the abnormal blood vessel and reduce the rate of blood flow through the abnormal blood vessel.

77. A method for visualizing blood vessels in an animal using an endoscope comprising
    (a) administering intravenously a plurality of boluses of from about 0.1 to about 1.0 ml of a liquid composition comprising a fluorescent dye and a carrier to the animal;
    (b) inserting an endoscope into the animal in a location adjacent the blood vessels desired to be visualized, wherein the endoscope includes a first instrument capable of emitting energy of a type and in an amount sufficient to cause the dye to fluoresce as the dye flows through the blood vessels and a second instrument capable of enabling angiographic images of the blood vessels to be obtained;
    (c) activating the first instrument to apply energy of a type and in an amount sufficient to cause the dye to fluoresce as the dye flows through the blood vessels; and
    (d) activating the second instrument to obtain an angiographic image of the fluorescing dye through the endoscope as the dye flows through the blood vessels, wherein step (c) is undertaken after each administration of the liquid composition.

78. The method of claim 77, wherein the dye consists essentially of indocyanine green and is present at a concentration of at least about 20 mg/ml.

79. The method of claim 78, wherein the indocyanine dye is present at a concentration of at least about 30 mg/ml.

80. A method for locating and treating a tumor in or adjacent to tissue defining a body cavity of an animal comprising
    (a) administering intravenously a liquid composition comprising a fluorescent dye and a carrier into the animal;
    (b) applying energy of a type and in an amount sufficient to cause the dye to fluoresce as the dye flows through the blood vessels of the body cavity tissue;
    (c) obtaining a plurality of angiographic images of the fluorescing dye using video camera as the dye enters and flows through the blood vessels of the body cavity tissue;
    (d) analyzing the angiographic images obtained in step (c) to determine whether a tumor is present in or adjacent to the body cavity tissue and the location of any blood vessel that feeds blood into the tumor; and
    (e) applying to any blood vessel located in step (d) that feeds blood into the tumor energy of a type and in an amount sufficient to excite the dye in the blood vessel and reduce the rate of blood flow through the vessel carrying blood into the tumor.

81. The method of claim 80, wherein in step (a) a plurality of boluses of from about 0.1 to about 1.0 ml of the liquid dye composition are administered to the animal, and wherein step (c) is undertaken after each administration of the liquid dye composition.

82. The method of claim 81, wherein the dye administered in step (a) consists essentially of indocyanine green and is present at a concentration of at least about 20 mg/ml.

83. The method of claim 82, wherein the indocyanine dye administered in step (a) is present at a concentration of at least about 30 mg/ml.

* * * * *